(12) United States Patent
Mongrenier

(10) Patent No.: US 10,733,397 B2
(45) Date of Patent: Aug. 4, 2020

(54) METHOD FOR MANAGING AT LEAST ONE CONTAINER AND ASSOCIATED METHODS AND DEVICES

(71) Applicant: BIOLOG-ID, Paris (FR)

(72) Inventor: Jean-Claude Mongrenier, Versailles (FR)

(73) Assignee: BIOLOG-ID, Boulogne Billancourt (FR)

( * ) Notice: Subject to any disclaimer, the term of this patent is extended or adjusted under 35 U.S.C. 154(b) by 0 days.

(21) Appl. No.: 16/340,806

(22) PCT Filed: Oct. 24, 2016

(86) PCT No.: PCT/EP2016/075513
§ 371 (c)(1),
(2) Date: Apr. 10, 2019

(87) PCT Pub. No.: WO2018/068872
PCT Pub. Date: Apr. 19, 2018

(65) Prior Publication Data
US 2019/0251309 A1    Aug. 15, 2019

(30) Foreign Application Priority Data
Oct. 11, 2016   (FR) ...................... 16 59827

(51) Int. Cl.
*H04Q 5/22*  (2006.01)
*G06K 7/10*  (2006.01)
(Continued)

(52) U.S. Cl.
CPC ....... *G06K 7/10366* (2013.01); *A61M 1/0286* (2014.02); *A61M 1/3693* (2013.01);
(Continued)

(58) Field of Classification Search
CPC .......... G06K 7/10366; G06K 7/10356; G06K 19/07767; A61M 1/3693; A61M 1/0286;
(Continued)

(56) References Cited

U.S. PATENT DOCUMENTS 7,776,601 B2    8/2010  De Gaulle et al.
10,402,711 B1 *  9/2019  Yamamoto ......... G06K 19/0723
(Continued)

FOREIGN PATENT DOCUMENTS

| EP | 3 076 339 A1 | 10/2016 |
| FR | 2 826 637 A1 | 12/2002 |
| WO | 2016/065113 A1 | 4/2016 |

OTHER PUBLICATIONS

International Search Report, dated Jul. 12, 2017, from corresponding PCT/EP2016/075513 application.

*Primary Examiner* — Tanmay K Shah
(74) *Attorney, Agent, or Firm* — Young & Thompson

(57) ABSTRACT

Disclosed is a method for managing at least one container containing a biological product, including the following steps: providing at least one container provided with a label, the label being a wireless communication chip capable of communicating according to a UHF mode and according to a HF mode, the chip being capable of transmitting or receiving a signal having a frequency of between 300 MHz and 3000 MHz in the UHF mode and having a frequency of between 3 MHz and 30 MHz in the HF mode, the label further including a memory; and reading at least one piece of information included in the memory, by a reader, the chip communicating with the reader according to the UHF mode or the HF mode.

11 Claims, 2 Drawing Sheets

(51) Int. Cl.
*A61M 1/02* (2006.01)
*G06K 19/077* (2006.01)
*A61M 1/36* (2006.01)
*A61J 1/10* (2006.01)

(52) U.S. Cl.
CPC ... *G06K 7/10356* (2013.01); *G06K 19/07767* (2013.01); *A61J 1/10* (2013.01); *A61J 2205/60* (2013.01); *A61M 2205/3592* (2013.01); *A61M 2205/52* (2013.01); *A61M 2205/6009* (2013.01)

(58) Field of Classification Search
CPC ...... A61M 2205/6009; A61M 2205/52; A61M 2205/3592; A61J 2205/60; A61J 1/10
USPC ...................................... 340/10.51
See application file for complete search history.

(56) References Cited

U.S. PATENT DOCUMENTS

| | | | | |
|---|---|---|---|---|
| 2008/0208750 A1* | 8/2008 | Chen | ............... | G06Q 10/087 705/50 |
| 2009/0189816 A1 | 7/2009 | Nikitin et al. | | |
| 2010/0253519 A1* | 10/2010 | Brackmann | ............... | B60P 3/03 340/572.1 |
| 2010/0265068 A1* | 10/2010 | Brackmann | ............... | B60P 3/03 340/572.1 |

* cited by examiner

METHOD FOR MANAGING AT LEAST ONE CONTAINER AND ASSOCIATED METHODS AND DEVICES

The present invention relates to a method for managing at least one container containing a biological product. The present invention also relates to a transmission method, a tracking method, a management device and a computer program product associated with the preceding methods.

BACKGROUND OF THE INVENTION

The present invention relates to the field of container logistics.

Such containers are for example pouches containing biological products such as blood products (pouches of primary blood, plasma, platelets, red blood cells, etc.) or cellular engineering products (stem cells, etc.), or drug pouches such as chemotherapy pouches.

The logistics of such containers require not only guaranteeing minimal exposure of the containers to a relatively high temperature, but also guaranteeing the confidentiality of certain information.

Indeed, for certain biological products, laws require a maximal exposure time of the containers to a temperature greater than −4° C. This maximum time is set in Europe at 2 hours and 30 minutes by a directive.

Regarding confidentiality, as an example, the patient for whom the container is intended in case of transfusion is not public information. There is therefore cause to develop a method making it possible to prevent an unauthorized person from collecting all of the information relative to the containers easily.

There is therefore a need for a method for managing at least one container containing a biological product allowing fast processing of a set of containers while allowing protection of the data associated with the container.

SUMMARY OF THE INVENTION

According to the invention, this aim is achieved by a method for managing at least one container containing a biological product, comprising the following steps: providing at least one container, the container being provided with a label, the label being a wireless communication chip capable of communicating according to a first operating mode called UHF mode and according to a second operating mode called HF mode, the chip being capable of transmitting or receiving a signal having a frequency of between 300 MHz and 3000 MHz in the UHF mode and capable of transmitting or receiving a signal having a frequency of between 3 MHz and 30 MHz in the HF mode, the label further comprising a memory comprising information and reading at least one piece of information included in the memory of the label, by a reader, the chip communicating with the reader according to the UHF mode or the HF mode.

According to specific embodiments, the management method includes one or more of the following features, considered alone or according to any technically possible combinations:

the method comprises the following steps: so-called UHF reading, in which a first reader having a given range reads all of the labels present within the range, the labels communicating with the first reader according to the UHF mode, and so-called HF reading, in which a second reader reads a single label at a time, the label communicating with the second reader according to the HF mode.

the label communicates a first part of the information during the UHF reading and a second part of the information during the HF reading, the second part not being included in the first part.

the first part of the information does not contain information relative to the origin of the biological product.

the communication between the chip and the reader according to the HF mode is implemented with the NFC protocol.

The invention also relates to a method for transmitting information from a parent container to a plurality of daughter containers, the method comprising the following steps: providing a parent container containing a biological product, managing the parent container by carrying out a management method applied to the parent container as previously defined to obtain information relative to the parent container, centrifuging the parent container using a centrifuge provided with the UHF reader, the UHF reader detecting the presence of the parent container during the centrifugation by communication with the label of the parent container according to the UHF mode, separating components of the biological product into a plurality of daughter containers, and writing, on each memory of the labels of the daughter containers, information relative to the parent container and information relative to the centrifugation owing to communication according to the HF mode.

The invention further relates to a method for tracking containers in an enclosure with a controlled atmosphere, comprising the following steps: providing a controlled-atmosphere enclosure having a plurality of compartments each delimiting an inner volume, the enclosure being equipped with at least one UHF reader, containers being placed in various determined locations, managing the containers by carrying out the management method applied to the containers as previously defined, comprising reading all of the labels of the containers in each compartment using the corresponding UHF reader, and tracking a location for each container present in the enclosure, the location corresponding to the corresponding UHF reader.

The invention further relates to a device for managing at least one container containing a biological product, comprising a reader and at least one container, the container being provided with a label, the label being a wireless communication chip capable of communicating according to a first operating mode called UHF mode and according to a second operating mode called HF mode, the chip being capable of transmitting or receiving a signal having a frequency of between 300 MHz and 3000 MHz in the UHF mode and capable of transmitting or receiving a signal having a frequency of between 3 MHz and 30 MHz in the HF mode, the label further comprising a memory comprising information, the chip being capable of communicating with the reader according to the UHF mode or the HF mode.

The invention also relates to an assembly comprising a so-called HF reader, capable of receiving a signal having a frequency of between 3 MHz and 30 MHz, and a controlled-atmosphere enclosure having a plurality of compartments each delimiting an inner volume, each compartment being equipped with a so-called UHF reader capable of receiving a signal having a frequency of between 300 MHz and 3000 MHz.

The invention further relates to a computer program product capable of carrying out at least one step of a method as previously described.

BRIEF DESCRIPTION OF THE DRAWINGS

Other features and advantages of the invention will appear upon reading the following description of embodiments of the invention, provided as an example only and in reference to the drawings, which are.

DETAILED DESCRIPTION OF THE PREFERRED EMBODIMENTS

Figure 1:
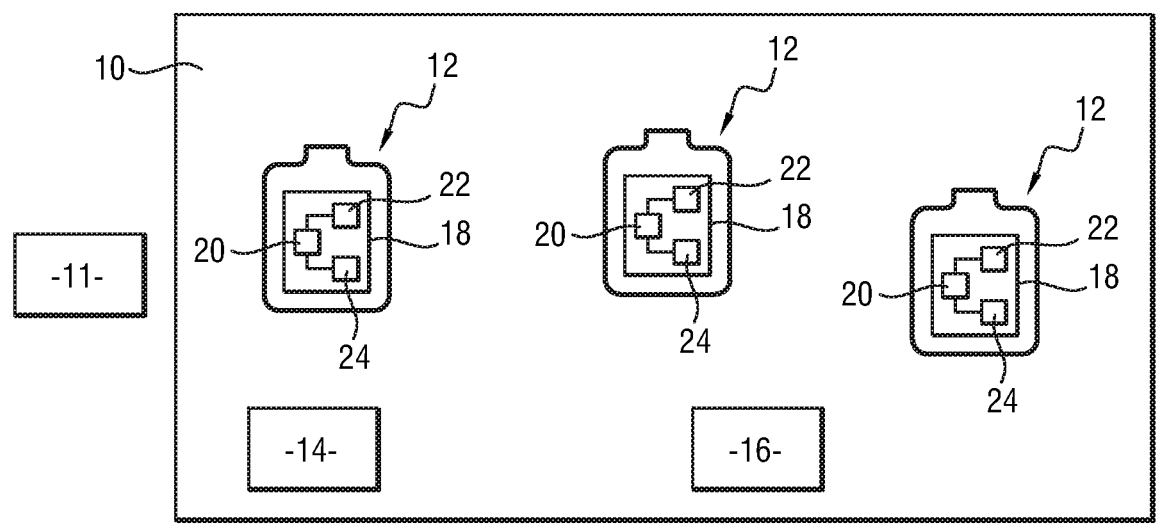
FIG. 1, a schematic illustration of a management device.

A management device 10, simply referred to as device 10 hereinafter, is shown in FIG. 1.

The device 10 includes a computer 11, three containers 12, a first reader 14 and a second reader 16.

According to other embodiments, the device 10 includes a different number of containers 12 and/or a different number of readers 14, 16.

In all of the embodiments, the device 10 includes at least one container 12 and one reader 14, 16.

The computer 11 is able to carry out a method for managing at least one container 12.

Alternatively, the computer 11 is a processing unit interacting with a computer program product to carry out instructions contained in the computer program product and making it possible to carry out a method for managing at least one container 12.

"Manage" refers both to an inventory issue (number of containers 12) and an identification issue, i.e., associating a container 12 with specific information, in particular relative to the content of the container 12.

Each container 12 includes biological products.

Generally, the container 12 is any type of pouch intended to contain products whose use is subject to strict storage constraints.

In one embodiment, the containers 12 are pouches containing biological products such as blood products (pouches of primary blood, plasma, platelets, red blood cells, etc.) or cellular engineering products (human or animal cells, in particular human or animal stem cells, products from human or animal cells).

In another embodiment, the containers 12 are drug pouches or therapeutic preparation pouches containing one or more active ingredients or medicaments, such as chemotherapy pouches (generally containing a solute and one or more chemotherapy active ingredients).

More generally, the container 12 is able to contain any product designed to be infused in a patient (human or animal).

According to the considered example, each container 12 is a pouch intended, in the present case, to contain blood products.

In a known manner, such a container 12 is a tight product container made from a breathable plastic material allowing metabolism, of the PVC (polyvinyl chloride), polycarbonate or PEG (polyethylene glycol) type.

The container 16 includes several faces and is provided with a label 18.

According to the illustrated example, the label 18 is an adhesive label that is adhered onto a face of the package 12.

The label 18 is a wireless communication chip.

The label 18 includes a radiofrequency antenna 20, a memory 22 and a microprocessor 24.

The label 18 is a label able to operate according to two separate frequency ranges. In this sense, the wireless communication chip can be described as a dual-frequency chip.

On the one hand, the label 18 is able to communicate according to a first operating mode called UHF mode. The acronym "UHF" stands for ultrahigh frequency.

In such a mode, the label 18 is able to transmit or receive a signal having a frequency of between 300 MHz and 3000 MHz.

On the other hand, the label 18 is able to communicate according to a second operating mode called HF mode. The acronym "HF" stands for high frequency.

In such a mode, the label 18 is able to transmit or receive a signal having a frequency of between 3 MHz and 30 MHz.

Each label 18 is associated with a unique identifier.

The unique identifier is stored in the memory 20.

The memory 22 for example comprises the following information: the unique identifier, an order number, the nature of the product contained in the container, a category of the product, for example, the immunological category, the name or an identifier of a patient to receive the perfusion and/or a control datum.

The antenna 20 makes it possible to send or receive signals.

The microprocessor 24 is able to communicate according to a first protocol and a second protocol separate from the first protocol.

The first protocol is for example compliant with standards ISO14443 or ISO15693. The second protocol is for example compliant with standards ISO18000-6C, also known as EPC1Gen2.

The microprocessor 24 is further capable of implementing a certain number of special commands due to the management of the two protocols.

The description provided above of a container 12 applies for all of the containers 12.

The first reader 14 is a reader able to communicate with a label 18 according to the UHF mode.

The first reader 14 has a communication range.

The communication range of the first reader 14 is preferably greater than 1 meter (m), more particularly between 5 meters and 10 meters.

The second reader 16 is a reader able to communicate with a label 18 according to the HF mode.

The communication between the chip and the reader according to the HF mode is implemented with a NFC protocol. "NFC" stands for "near-field communication". According to one particular example, the communication protocol is according to standards ISO 14443, ISO 15693 or ISO 18000-3m.

The second reader 16 has a communication range.

The communication range of the second reader 16 is preferably less than 20 centimeters (cm).

The space between the label 18 and the second reader 16 thus corresponds to a detection distance.

Furthermore, the second reader 16 is able to power the label 18 in HF mode.

The operation of the device 10 is now described in reference to one example embodiment of a management method of at least one container 12 containing a biological product.

The management method includes a step for providing a container 12 bearing a label 18.

The management method also includes a step for reading of at least one piece of information included in the memory of the label by a reader 14 or 16.

During the reading, the label 18 communicates with the reader 14 or 16 according to the UHF mode or the HF mode.

According to one example, the management method comprises so-called UHF reading.

A first reader 14 reads all of the labels 18 present within range of the first reader 14, the labels communicating with said reader according to the UHF mode.

During the UHF reading, the label 18 communicates a first part of the information of the memory, for example comprising the unique identifier.

This for example makes it possible to identify all of the containers 12 quickly at a given distance.

Alternatively or additionally, the management method comprises so-called HF reading.

The second reader 16 reads a single label 18 at a time, the label 18 communicating with the reader according to the HF mode.

During the HF reading, the label 18 communicates a second part of the information of the memory 22 of the label 18.

The second part of the information of the memory 22 is not included in the first part, i.e., there is at least one piece of information included in the memory that is capable of being communicated by HF reading but not by UHF reading.

The pieces of information not included in the first part of the memory 22 are for example the identification of a patient to be perfused, the destination of a container 12 during a transfer.

The UHF reading and the HF reading are for example done simultaneously.

Such a management method makes it possible to distinguish a given container 12 from another container 12, which does not necessarily contain the same product. More particularly, this allows a medical professional to verify the identifier of the container 12 and the nature of the product contained in the container 12 before perfusing a patient with the container 12 by reading the label of said container 12.

The management method in particular makes it possible to secure private information, such that it is not easily possible to recover the private information of a plurality of containers quickly. A person wishing to know this private information must have close access to the containers 12 and must read each label 18 by HF mode.

The use of a dual-frequency chip in managing containers 12 containing a biological product thus makes it possible to provide tracking of the containers 23, allowing both fast reading of a set of labels and protection of private data.

Furthermore, the same particular allows quick location tracking and more specific location. The medical personnel therefore knows a location of the desired containers to save time and maintain the storage conditions of the containers 12.

Figure 2:
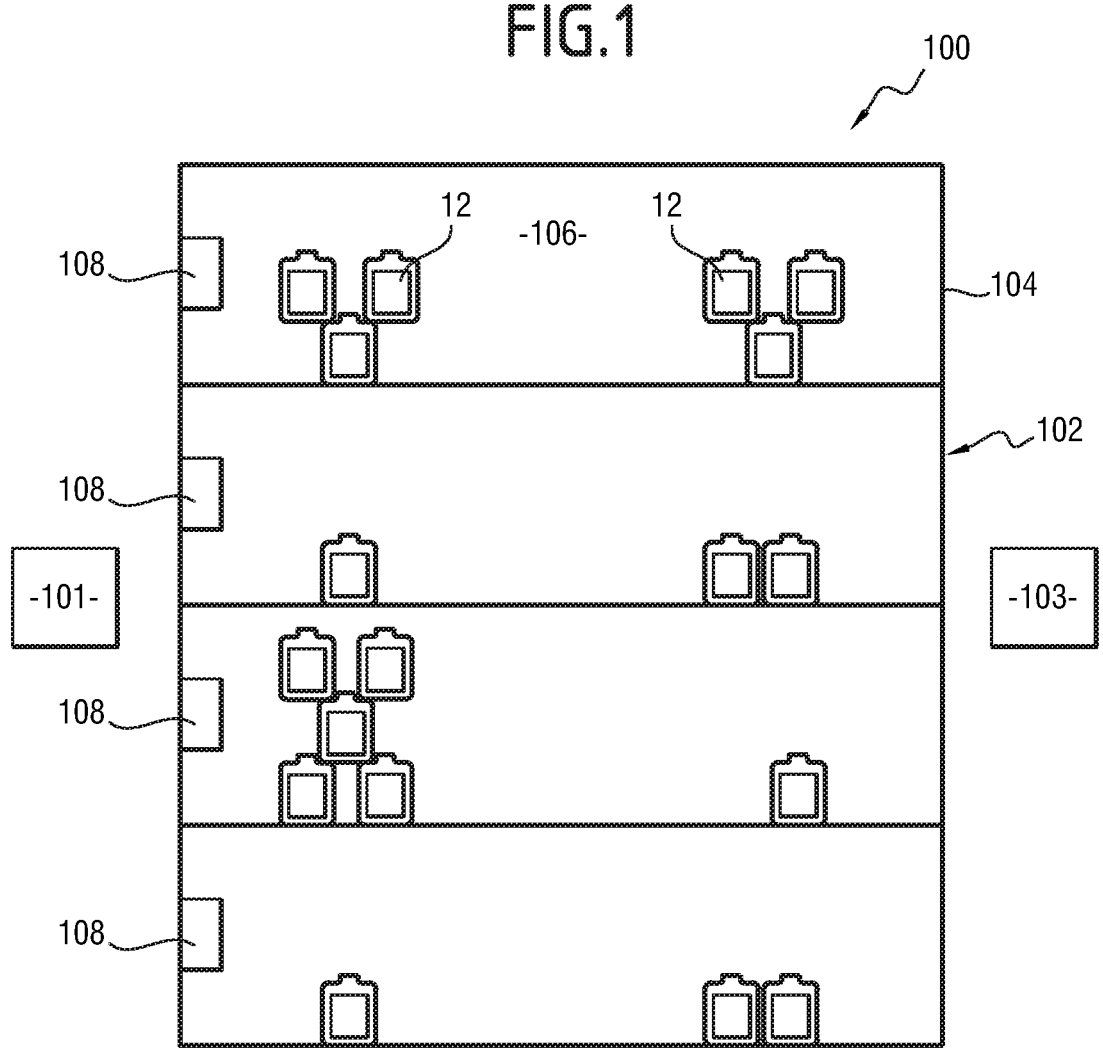
FIG. 2, a schematic illustration of a controlled-atmosphere enclosure.

Such an idea is also used in the assembly 100 shown in FIG. 2.

The assembly 100 includes a computer 101, an enclosure 102 and a reader 103.

The computer 101 is able to implement methods, such as a method for tracking containers 12 or for transmitting information between containers 12.

The enclosure 102 is an enclosure 102 intended to receive containers 12 in a controlled atmosphere.

An atmosphere is qualified as "controlled" when at least one parameter of the atmosphere is regularly controlled. The parameter is, depending on the case, the temperature, pressure or the humidity.

To that end, the enclosure 102 is usually called controlled-atmosphere enclosure.

The enclosure 102 is for example a refrigerator or an agitator.

The controlled-atmosphere enclosure 102 has a plurality of compartments 104 each delimiting an inner volume 106.

The compartments 102 are able to receive containers 12 in the inner volume 106. In a first embodiment, each compartment 104 includes walls shielded so that the signals having a frequency of between 3 MHz and 3000 MHz are not able to enter or leave the compartment 104.

Each wall of the compartment 104 is for example made from non-ferromagnetic metal, in particular aluminum, copper or stainless steel, in particular according to European standard EN 10027 X5CrNi18-10 1.4301 corresponding to American Standard AISI 304.

Each wall has a thickness greater than three thicknesses of skin. The thickness is determined based on the nature of the material of the wall and the frequency of the signals that one wishes to block.

In one embodiment, each wall is made from aluminum with a thickness equal to 150 μm. This in particular makes it possible to block the signals having a frequency equal to 3 MHz. Furthermore, a thickness of 66 μm of aluminum is capable of blocking the signals having a frequency equal to 13.56 MHz.

Alternatively, each wall is made from copper with a thickness equal to 100 μm in order to block the signals having a frequency equal to 3 MHz or a thickness equal to 50 μm in order to block the signals having a frequency equal to 13.56 MHz.

Alternatively, each wall is made from stainless steel with a thickness equal to 700 μm in order to block the signals having a frequency equal to 3 MHz or a thickness equal to 360 μm in order to block the signals having a frequency equal to 13.56 MHz.

In one variant, the compartments are spaced apart from one another, the signals having a frequency of between 3 MHz and 3000 MHz not being able to propagate from one compartment 104 to another compartment 104.

The space between two compartments 104 is then large enough for the attenuation of the signals at a frequency of between 3 MHz and 3000 MHz during their propagation between two compartments 104 to make it possible to disregard the possibility of detecting the signals coming from another compartment 104.

Each compartment 104 is equipped with its own reader 108 separate from the HF reader 101.

Each reader 108 of a compartment 104 is able to receive a signal having a frequency of between 300 MHz and 3000 MHz.

Hereinafter, each reader 108 is called UHF reader 108.

In a second embodiment, a signal having a frequency of between 3 MHz and 3000 MHz is capable of circulating in the enclosure 102. The enclosure 102 then for example has a single UHF reader.

The reader 103 is a reader similar to the second reader 16.

Therefore, hereinafter, the reader 103 is called HF reader 103.

The operation of the assembly 10 is now described in reference to an example embodiment of a method for tracking containers 12 in the enclosure 102.

The tracking method includes a step for providing the enclosure 102, containers 12 being placed in various determined locations.

The tracking method then includes an implementation of the management of the containers 12 by the implementation of the management method previously described applied to the containers 12.

In particular, the step for managing the containers 12 comprises reading of the set of labels 18 of the containers 12 in each compartment 104 by the corresponding UHF reader 108.

The UHF reader 108 has a range comprising all of the interior volume 106 able to be occupied by containers 12.

Thus, during the management, the UHF reader(s) 108 detect all of the labels 18 of the containers 12 in the enclosure 102.

The tracking method also includes a step for tracking the location of each container 12.

The nature of the tracking depends on the cases.

As an example, the UHF reader(s) 108 and the HF reader 103 of the enclosure 102 transmit, to the computer 101, pieces of information relative to the detected containers 12, for example, the identifier of the containers 12 and the nature and optionally the category of their contents.

Thus, the computer 101 is able to compute and display the number of remaining containers 12 containing contents of a certain nature and/or category. In the case of blood pouches, the computer 101 displays the number of containers by blood group, or by rhesus.

The computer 101 is for example capable of sending an alert when the number of containers containing contents of a certain nature and/or category is below a threshold. For example, when the number of containers in blood group O is below a determined threshold, the computer 101 sends an alert, blood group O serving as emergency blood group and being a priori compatible with all patients.

According to another example, the location tracking makes it possible to obtain the location of the container 12.

According to one embodiment that is not shown, each compartment 104 further includes an HF antenna.

The computer 101 is able to determine whether the chip is detected by an HF antenna or a UHF antenna.

For each container 12, at least one HF antenna is activated alternately until an HF antenna detects the presence of a corresponding label 18.

More particularly, to accelerate the location, the detection is done by dichotomy: a first half of the HF antennas is first activated, if the label 18 is detected by the first half, then half of the first half of the HF antennas is activated, otherwise half of the second half of the HF antennas is activated. One continues in this way until only one HF antenna is activated and it is possible to deduce therefrom which antenna is able to detect the presence of the label.

The location of the container 12 corresponds to the HF antenna detecting the label.

The location of the container 12 is comprised in the location associated with said HF antenna.

Figure 3:
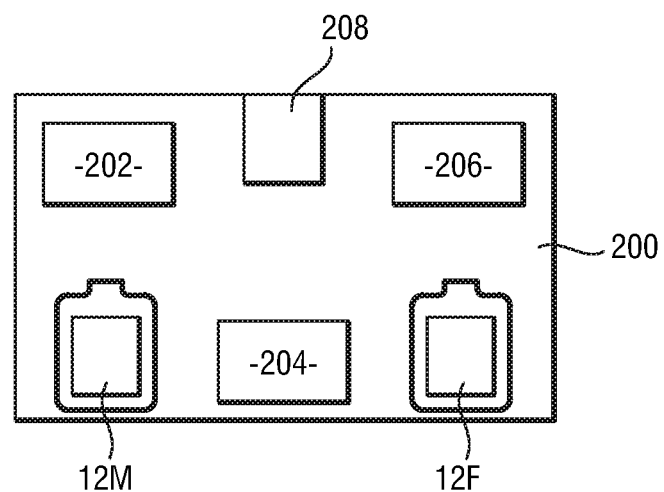
FIG. 3, a schematic illustration of a centrifuge.

FIG. 3 describes a centrifuge 200 provided with a computer 202, a UHF reader 204, a centrifugation unit 206 and a writing means 208.

The computer 202 is able to implement a method for transmitting information from a parent container 12M to a plurality of daughter containers 12F.

Each parent container 12M or each daughter container 12F includes a label 18 as previously described.

The UHF reader 204 is similar to the UHF readers previously described.

The centrifugation unit 206 guarantees the formation of the daughter containers 12F from the parent container 12M.

The writing means 208 is a member capable of writing on labels 18.

The operation of the centrifuge 200 is now described in reference to an example embodiment of a method for transmitting information on a parent container 12M to a plurality of daughter containers 12F.

The transmission method includes a step for providing a parent container 12M containing a biological product.

The transmission method includes a step for managing the parent container 12M.

The step for managing the parent container 12 corresponds to the implementation of the management method previously described applied to the parent container 12M.

The management method applied to the parent container 12M for example comprises a reading step HF.

The management step makes it possible to obtain information relative to the parent container 12M.

The transmission method then includes a step for centrifugation of the parent container 12M.

During the centrifugation, the UHF reader 204 detects the presence of the parent container 12F by communication with the label of the parent container 12F according to the UHF mode.

The use of the UHF in particular makes it possible to track the parent container 12M in the centrifuge, including during rotation. Thus, the UHF reader 204 is able to verify that the container 12 has stayed in the centrifugation unit 206 throughout the entire centrifugation step.

The transmission method next comprises a step for separating components of the biological product into a plurality of daughter containers 12F.

The transmission method lastly includes a step for writing on each memory 22 of the labels 18 of the daughter containers 12F.

In a memory 22 of the labels 18 of the daughter containers 12F, information relative to the parent container 12M and information relative to the centrifugation is written owing to communication in the HF mode.

This allows tracking between the parent container 12M and the daughter containers 12F.

More generally, in each of the embodiments, the use of a dual-frequency label in managing containers 12 containing a biological product thus makes it possible to provide tracking of the containers 12, allowing both fast reading of a set of labels 18 and protection of private data.

More specifically, the use of a dual-frequency label offers the user the advantage of benefiting according to the contexts from the advantages of one technique relative to another. In some uses, the speed of the UHF mode must be favored, while in others, it is the precision of the HF mode that should be favored.

The invention claimed is:

1. A method for managing at least one container containing a biological product, comprising steps of:
   providing at least one container, the container being provided with a label and the label being a wireless communication chip configured to communicate in a first operating mode in accordance with a UHF mode, and also configured to communicate in a second operating mode in accordance with an HF mode, the communication chip being further configured to transmit and receive signals having a frequency of between 300 MHz and 3000 MHz in the UHF mode, and to transmit and receive signals having a frequency of between 3 MHz and 30 MHz in the HF mode, the label further comprising a memory with information stored thereon;
   UHF reading, in which a first reader having a given range reads all labels present within the range, the labels communicating with the first reader according to the UHF mode; and HF reading, in which a second reader reads one label of said labels, the one label communicating with the second reader according to the HF mode, wherein the second reader reads from the memory of the one label at least one piece of information that is not accessible by reading in the UHF mode.

2. The management method according to claim 1, wherein communication between the communication chip and the second reader according to the HF mode is implemented with NFC protocol.

3. A non-transitory computer-readable medium on which is stored a computer program, which when executed by a computer, carries out at least one step of a method according to claim 1.

4. A method for managing at least one container containing a biological product, comprising steps of:
providing one or more containers, each container of said containers being provided with a label and the label being a wireless communication chip configured to communicate in a first operating mode in accordance with a UHF mode, and also configured to communicate in a second operating mode in accordance with an HF mode, the communication chip being further configured to transmit and receive signals having a frequency of between 300 MHz and 3000 MHz in the UHF mode, and to transmit and receive signals having a frequency of between 3 MHz and 30 MHz in the HF mode, the label further comprising a memory with information stored thereon;
UHF reading, in which a first reader having a given range reads all labels present within the range, each one of the labels communicating with the first reader according to the UHF mode; and
HF reading, in which a second reader reads one label at a time, and the one label communicates with the second reader according to the HF mode.

5. The management method according to claim 4, wherein the one label communicates a first part of the information during the UHF reading, and communicates a second part of the information during the HF reading, the second part not being included in the first part.

6. The management method according to claim 5, wherein the first part of the information does not contain information relative to an origin of the biological product.

7. The management method according to claim 4, wherein communication between the communication chip and the reader according to the HF mode is implemented with NFC protocol.

8. A method for transmitting information from a parent container to a plurality of daughter containers, the method comprising steps of:
providing a parent container containing a biological product, the parent container being provided with a label and the label being a wireless communication chip configured to communicate in a first operating mode in accordance with a UHF mode, and also configured to communicate in a second operating mode in accordance with an HF mode, the communication chip being further configured to transmit and receive signals having a frequency of between 300 MHz and 3000 MHz in the UHF mode, and to transmit and receive signals having a frequency of between 3 MHz and 30 MHz in the HF mode, the label further comprising a memory with information stored thereon;
centrifuging the parent container using a centrifuge provided with a UHF reader, the UHF reader detecting a presence of the parent container during centrifugation by communication with the label of the parent container according to the UHF mode;
separating components of the biological product into a plurality of daughter containers; and
writing, on memory of each of the labels of the daughter containers, information relative to the parent container and information relative to the centrifugation owing to communication according to the HF mode.

9. A method for tracking containers in an enclosure with a controlled atmosphere, comprising steps of:
providing a controlled-atmosphere enclosure having a plurality of compartments each delimiting an inner volume, the enclosure being equipped with a UHF reader, and containers being placed in various determined locations within the enclosure, the containers each being provided with a label and the label being a wireless communication chip configured to communicate in a first operating mode in accordance with a UHF mode, and also configured to communicate in a second operating mode in accordance with an HF mode, the communication chip being further configured to transmit and receive signals having a frequency of between 300 MHz and 3000 MHz in the UHF mode, and to transmit and receive signals having a frequency of between 3 MHz and 30 MHz in the HF mode, the label further comprising a memory with information stored thereon;
reading labels of all the containers in each compartment of the enclosure using the UHF reader, the communication chips of the labels communicating with the reader according to the UHF mode; and
tracking a location for each container present in the enclosure, the location corresponding to the UHF reader.

10. A device for managing at least one container containing a biological product, comprising:
a reader; and
at least one container, the container being provided with a label, the label being a wireless communication chip configured to communicate in a first operating mode in accordance with a UHF mode, and also configured to communicate in a second operating mode in accordance with an HF mode, the communication chip being further configured to transmit and receive signals having a frequency of between 300 MHz and 3000 MHz in the UHF mode, and to transmit and receive signals having a frequency of between 3 MHz and 30 MHz in the HF mode, the label further comprising a memory with information stored thereon, the communication chip being configured to communicate with the reader according to the UHF mode and the HF mode, and at least one piece of information of the memory being accessible with the HF mode and inaccessible with the UHF mode.

11. An assembly, comprising:
an HF reader configured to receive signals having a frequency of between 3 MHz and 30 MHz;
a controlled-atmosphere enclosure having a plurality of compartments each delimiting an inner volume, each compartment of said compartments being equipped with a UHF reader configured to receive signals having a frequency of between 300 MHz and 3000 MHz; and
containers placed in various determined locations within the enclosure,
each container being provided with a label, the label being a wireless communication chip configured to communicate in a first operating mode in accordance with a UHF mode, and also configured to communicate in a second operating mode in accordance with an HF mode, the communication chip being further configured to transmit and receive signals having a frequency of between 300 MHz and 3000 MHz in the UHF mode, and to transmit and receive signals having a frequency of between 3 MHz and 30 MHz in the HF mode, the label further comprising a memory with information stored thereon, wherein, in the UHF mode, a first reader having a given range is adapted to read all of labels of the one or more containers present within the range, and wherein, in the HF mode, a second reader is adapted to read one label of the labels, including at least one piece of information of the memory of the one label that is accessible in the HF mode and inaccessible via the UHF mode.

\* \* \* \* \*